(12) United States Patent
Kara et al.

(10) Patent No.: US 11,318,051 B2
(45) Date of Patent: May 3, 2022

(54) HEARING PROTECTION DEVICES, NOISE EXPOSURE SENSORS THEREFOR, AND SENSOR HOUSINGS AND ASSOCIATED METHODS FOR THE SAME

(71) Applicant: HONEYWELL INTERNATIONAL INC., Morris Plains, NJ (US)

(72) Inventors: Peter Kara, Morris Plains, NJ (US); Erik Pertot, Morris Plains, NJ (US); Matthew Chen, Morris Plains, NJ (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 0 days.

(21) Appl. No.: 16/881,644

(22) Filed: May 22, 2020

(65) Prior Publication Data

US 2020/0368071 A1 Nov. 26, 2020

(30) Foreign Application Priority Data

May 24, 2019 (EP) .................................. 19176573

(51) Int. Cl.
*A61F 11/06* (2006.01)
*A61F 11/14* (2006.01)
(Continued)

(52) U.S. Cl.
CPC ............ *A61F 11/14* (2013.01); *H04R 1/1008* (2013.01); *H04R 1/288* (2013.01); *H04R 1/2876* (2013.01); *H04R 29/004* (2013.01); *A61F 11/145* (2022.01)

(58) Field of Classification Search
CPC ...... A61F 11/06; A61F 11/14; A61F 2011/145
(Continued)

(56) References Cited

U.S. PATENT DOCUMENTS 5,491,747 A * 2/1996 Bartlett .................. H04M 1/19
379/433.03
6,297,792 B1 10/2001 Takahashi
(Continued)

FOREIGN PATENT DOCUMENTS

WO 2006/118516 A1 11/2006

OTHER PUBLICATIONS

Extended European Search Report for Patent Application No. 19176573.4 dated Dec. 17, 2019, 7 pages.
(Continued)

*Primary Examiner* — Katherine A Faley
(74) *Attorney, Agent, or Firm* — Alston & Bird LLP

(57) ABSTRACT

Disclosed are hearing protection devices and housings for noise sensors for the same. Hearing protection devices can include an ear cup including an external casing partially defining an inner space, a noise sensor including a microphone electrically coupled to a printed circuit board, and a housing disposed in an aperture defined in the external casing. The housing can define an axial bore defining a noise sensor receiving portion and an acoustic communication portion. The inner space of the ear cup can be substantially airtight when the housing is sealably disposed at or proximate the aperture, the microphone is engaged within the noise sensor receiving portion of the housing, and the ear cup is worn securely about the wearer's ear. The noise sensor can be calibrated by removing a removable securing collar and slidably disposing a calibration tool into the axial bore without further disassembling the hearing protection device.

14 Claims, 8 Drawing Sheets

(51) Int. Cl.
*H04R 1/10* (2006.01)
*H04R 1/28* (2006.01)
*H04R 29/00* (2006.01)

(58) Field of Classification Search
USPC .......................................................... 381/72
See application file for complete search history.

(56) References Cited

U.S. PATENT DOCUMENTS

| | | |
|---|---|---|
| 8,934,638 B2 | 1/2015 | Kimura |
| 9,762,991 B2 | 9/2017 | Yang |
| 2002/0110256 A1* | 8/2002 | Watson ..................... B60R 1/12 |
| | | 381/389 |
| 2005/0094832 A1* | 5/2005 | Song ........................ H04R 1/06 |
| | | 381/174 |
| 2008/0187150 A1* | 8/2008 | Heringslack ........... H04R 1/086 |
| | | 381/72 |
| 2010/0303270 A1 | 12/2010 | Parkins |
| 2012/0314882 A1* | 12/2012 | Sibbald ................ H04R 1/1075 |
| | | 381/71.6 |
| 2018/0033422 A1 | 2/2018 | Sibbald |
| 2018/0041828 A1 | 2/2018 | Sibbald et al. |
| 2018/0288520 A1 | 10/2018 | Roberts |

OTHER PUBLICATIONS

Intention to grant issued in European Application No. 19176573.4 dated Jun. 23, 2021, 5 pages.
Office Action issued in Canadian Application No. 3081121 dated Jun. 22, 2021, 5 pages.

\* cited by examiner

HEARING PROTECTION DEVICES, NOISE EXPOSURE SENSORS THEREFOR, AND SENSOR HOUSINGS AND ASSOCIATED METHODS FOR THE SAME

CROSS-REFERENCE TO RELATED APPLICATIONS

This specification is based upon and claims the benefit of priority from European patent application number EP 19176573.4 filed on May 24, 2019, the entire contents of which are incorporated herein by reference.

BACKGROUND

In the field of hearing protection, hearing protection devices such as earmuffs are often used to protect a wearer's ears from excessive noise exposure. Such hearing protection devices often provide a passive and/or active noise dampening or noise cancellation effect for the wearer, often in an effort to reduce the total noise exposure for a wearer to below a regulated or suggested acute or chronic exposure limit. In such devices, one or more noise sensors can be placed in or about the hearing protection device. However, such noise sensors are often susceptible to damage from exposure to dust and other contaminants, often measure noise exposure in a manner that is not true to the wearer's actual exposure, are costly to manufacture, require significant space within the hearing device, and often cannot be calibrated reliably and/or without substantial disassembly of the hearing protection device. Through applied effort, ingenuity, and innovation, many of these identified problems have been solved by developing solutions that are included in embodiments of the present disclosure, many examples of which are described in detail herein.

SUMMARY

Apparatus, systems, and methods described herein relate to hearing protection devices and noise exposure sensor housings for the same. In some embodiments, the hearing protection device can include an ear cup including an external casing partially defining an inner space, a noise sensor including a microphone electrically coupled to a printed circuit board, and a housing disposed in an aperture defined in the external casing. The housing can define an axial bore defining a noise sensor receiving portion and an acoustic communication portion. The inner space of the ear cup can be substantially airtight when the housing is sealably disposed at or proximate the aperture, the microphone is engaged within the noise sensor receiving portion of the housing, and the ear cup is worn securely about the wearer's ear. The noise sensor can be calibrated by removing a removable securing collar and slidably disposing a calibration tool into the axial bore without further disassembling the hearing protection device.

In some embodiments, a noise sensor assembly for a hearing protection device can include a noise sensor comprising a microphone electrically coupled to a printed circuit board (PCB). In some embodiments, the noise sensor assembly can comprise a housing dimensioned and configured to be fixably disposed at or proximate an aperture defined in an outer surface of an external casing of the hearing protection device. In some embodiments, the housing can comprise an inner surface defining an axial bore. In some embodiments, a distal end of the axial bore is configured to acoustically communicate with an external environment via the aperture. In some embodiments, the housing can define a noise sensor receiving portion comprising a slot configured to engage the PCB of the noise sensor. In some embodiments, the slot of the housing is configured to retain the noise sensor, such that the microphone faces the axial bore. In some embodiments, in an instance in which the noise sensor is engaged with the housing, the noise sensor is sealed against the housing. In some embodiments, the axial bore of the housing is dimensioned and configured to slideably receive a calibration tool to form an airtight seal with the inner surface of the housing. In some embodiments, the housing can further define a securing portion at a distal end, the securing portion adapted to contact and secure the housing with respect to a portion of the outer surface of the hearing protection device. In some embodiments, the noise sensor assembly can further comprise an internal dust protector disposed between the noise sensor receiving portion of the housing and the noise sensor, and wherein the internal dust protector is disposed between the microphone and the axial bore. In some embodiments, the housing comprises at least one of a vibration attenuation material and a noise dampening material. In some embodiments, in an instance in which the noise sensor is engaged with the housing, the noise sensor is retained within the noise sensor receiving portion and abuts the slot.

In some embodiments, an ear cup for a hearing protection device is disclosed. In some embodiments, the hearing protection device can comprise an external casing defining an aperture. In some embodiments, the ear cup can comprise a noise sensor comprising a microphone electrically coupled to a printed circuit board (PCB) and a housing fixably disposed at or proximate the aperture defined by the external casing. In some embodiments, the housing can comprises an inner surface defining an axial bore. In some embodiments, a distal end of the axial bore is configured to acoustically communicate with an external environment via the aperture. In some embodiments, the housing defines a noise sensor receiving portion comprising a slot configured to engage the PCB of the noise sensor. In some embodiments, the slot of the housing is configured to retain the noise sensor, such that the microphone faces the axial bore. In some embodiments, in an instance in which the noise sensor is engaged with the housing, the noise sensor is sealed against the housing, and the noise sensor and the housing seal the aperture defined by the external casing. In some embodiments, the ear cup can further comprise a removable securing collar. In some embodiments, the external casing comprises a first portion and a second portion, the second portion defining the aperture configured to sealably retain the removable securing collar, the second portion configured to sealably engage the first portion such that the first portion, the second portion, and the removable securing collar seal the aperture in the external casing. In some embodiments, the noise sensor receiving portion of the axial bore has a first inner diameter and the distal end portion of the axial bore has a second inner diameter less than the first inner diameter. In some embodiments, the ear cup can further comprise a removable sealing collar configured to sealably retain the housing at or proximate the aperture defined by the external casing, the removable securing collar comprising an opening such that the distal end of the axial bore of the housing is configured to acoustically communicate with the external environment via the aperture of the external casing and the opening of the removable sealing collar. In some embodiments, the ear cup can further comprise a removable sealing collar configured to be retained by the aperture, wherein the axial bore of the housing is configured such that when the removable securing collar is removed and the calibration tool is slideably inserted into the axial bore of the housing, the calibration tool forms an airtight seal with an inner surface of the axial bore of the housing. In some embodiments, the ear cup can further comprise an external dust protector disposed between the housing and the removable securing collar. In some embodiments, the housing further comprises a securing portion disposed about the axial bore, the securing portion comprising a first securing portion at a distal end of the housing having a first outer diameter and a second securing portion proximal of the first securing portion, the second securing portion have a second outer diameter less than the first outer diameter, the first securing portion and the second securing portion defining a flange and recess configured to secure the housing relative to the external casing. In some embodiments, in an instance in which the noise sensor is engaged with the housing and the housing is sealably disposed directly or indirectly at or proximate the aperture of the external casing of the ear cup, and the ear cup is sealably engaged to a wearer's head about the wearer's ear, an internal volume of the ear cup is substantially airtight.

In some embodiments, a method for calibrating a noise sensor of a hearing protection device is described. In some embodiments, the hearing protection device can comprise an external casing defining an aperture, a noise sensor comprising a microphone electrically coupled to a printed circuit board (PCB) and a housing fixably disposed at or proximate the aperture defined by the external casing. In some embodiments, the housing of the hearing protection device can comprises an inner surface defining an axial bore. In some embodiments, a distal end of the axial bore of the housing of the hearing protection device can be configured to acoustically communicate with an external environment via the aperture. In some embodiments, the housing of the hearing protection device can define a noise sensor receiving portion comprising a slot configured to engage the PCB of the noise sensor. In some embodiments, the slot of the housing of the hearing protection device can be configured to retain the noise sensor, such that the microphone faces the axial bore. In some embodiments, in an instance in which the noise sensor is engaged with the housing of the hearing protection device, the noise sensor can be sealed against the housing and the noise sensor and the housing can seal the aperture defined by the external casing of the ear cup. In some embodiments, the ear cup can further comprise a removable securing collar configured to retain the noise sensor and/or the housing in place in or proximate the aperture. In some embodiments, the method can comprise at least disposing a calibration tool through the aperture via the axial bore of the housing such that an interior of the calibration tool and the microphone are part of a closed system. In some embodiments, the method can comprise emitting, by the calibration tool, a calibrating sound having predetermined sound characteristics. In some embodiments, the method can comprise receiving, using the microphone, one or more detected sound characteristics of the calibrating sound. In some embodiments, in an instance in which a comparison of the one or more detected sound characteristics of the calibrating sound received by the microphone and the sound characteristics of the calibrating sound is indicative of a calibration error, calibrating the noise sensor relative to the calibrating sound.

BRIEF DESCRIPTION OF THE DRAWINGS

The accompanying drawings, which constitute a part of the description, illustrate embodiments of the present invention and, together with the description thereof, serve to explain the principles of the present invention.

DETAILED DESCRIPTION

Figure 1A:
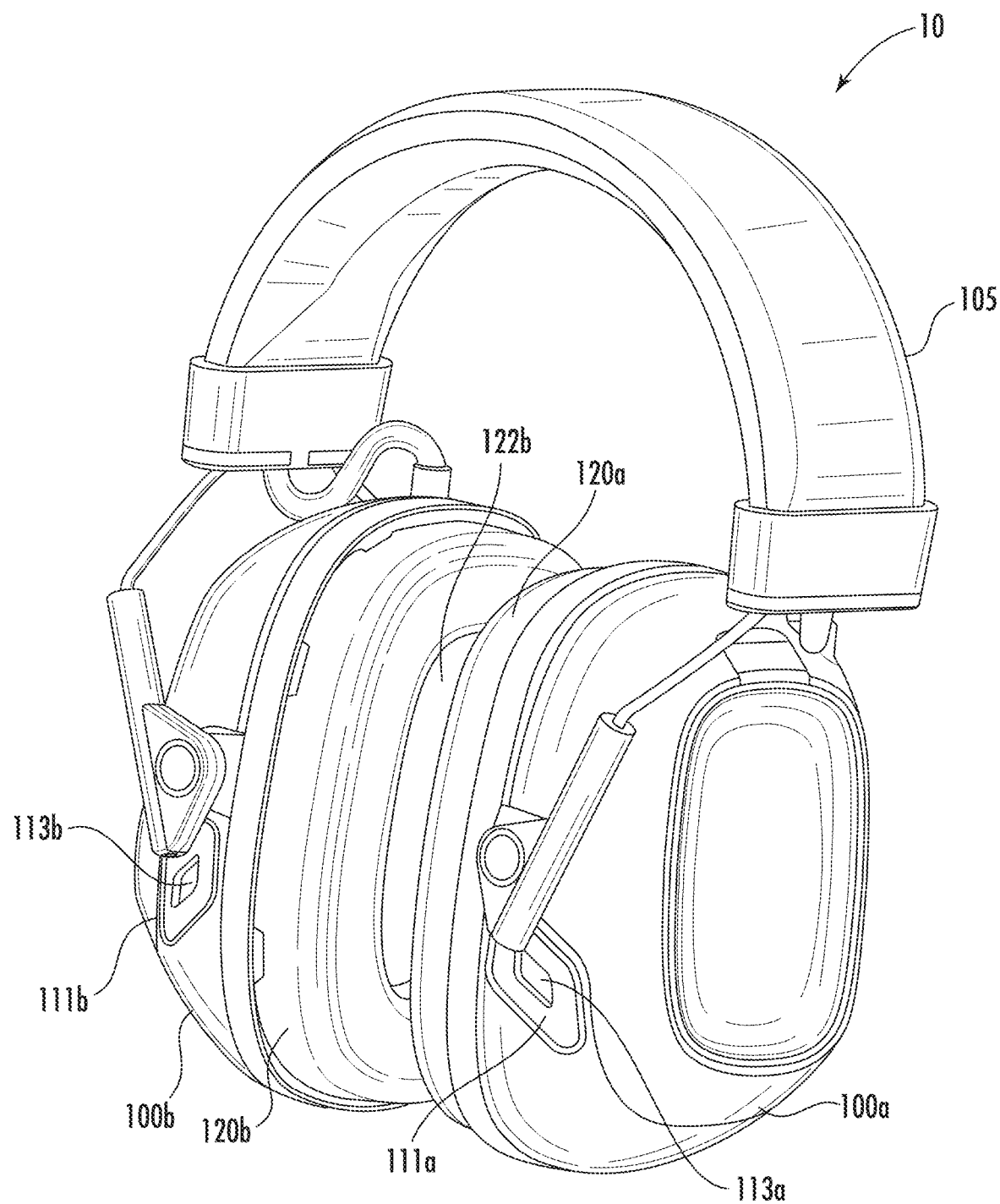
FIG. 1A shows a perspective view of a hearing protection device, according to an embodiment of the present invention.

It should be understood that although illustrative implementations of one or more embodiments are disclosed and discussed below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents. The following description of at least one exemplary embodiment is in fact merely illustrative and is in no way intended as a limitation to the present invention and its application or use.

Techniques and devices known to those of ordinary skill in the relevant art may not be discussed in detail but where appropriate, the techniques and devices should be considered as part of the description. Among all the examples shown and discussed herein, any specific value should be construed as merely illustrative and not as a limitation. Thus, other examples of exemplary embodiments may have different values. It should be noted that similar reference numerals and letters denote similar items in the accompanying drawings, and therefore, once an item is defined in a drawing, there is no need for further discussion in the accompanying drawings.

The following brief definition of terms shall apply throughout the application:

The term "comprising" means including but not limited to, and should be interpreted in the manner it is typically used in the patent context;

The phrases "in some embodiments," "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

In the field of hearing protection, hearing protection devices such as earmuffs may be used to protect a wearer's ears from excessive noise exposure. Such hearing protection devices may provide a passive and/or active noise dampening or noise cancellation effect for the wearer, often in an effort to reduce the total noise exposure for a wearer to below a regulated or suggested acute or chronic exposure limit. For instance, an 8 hour maximum daily exposure time may be associated with a noise exposure level of about 85 decibels (dBA), while a person may be limited to 2 hours of exposure time per day for a noise exposure level of 91 dBA, 30 minutes for a noise exposure level of 97 dBA, and seven minutes for a noise exposure level of 103 dBA. By wearing such hearing protection devices, a wearer is able to reduce their noise exposure level, thereby lengthening the maximum daily exposure time such that the wearer can, for example, remain in a higher ambient noise working environment for a longer period of time under such exposure limit regulations. In some embodiments discussed herein, to perform active noise cancellation and/or verify that the hearing protection device is effectively preventing noise exposure during use, one or more noise sensors can be placed in or about the hearing protection device (e.g., on or in an ear cup of a pair of earmuffs). Since these noise sensors must be quite small while also being effective, microelectromechanical system (MEMS) microphones can be used as the noise sensors. Embodiments of the present disclosure facilitate such noise sensors, and may reduce exposure to dust and other contaminants, may measure noise exposure in a manner that is true to the wearer's actual exposure, and may be calibrated reliably and/or without substantial disassembly of the hearing protection device while having a small footprint in the hearing protection device and being cost effective.

Microphones, such as MEMS microphones, for use as a noise exposure sensor in ear muffs or other such hearing protection can often comprise a vibrating diaphragm and a back electrode, forming a capacitor integrated on a silicon wafer, which thereby realizes the acoustic-electric conversion. Such a capacitive microphone may be provided with through holes on its back electrode in order to balance the pressure between the vibrating diaphragm and the back electrode. The microphone of such a structure, especially when the cavity about the microphone is sealed and filled with air, has higher acoustic impedance compared to the traditional microphone, and thereby has higher noise attenuation. Since a sealed, air-filled cavity about the microphone can be an important factor in achieving accurate detection of a calibrating noise during in situ calibration, such calibration of the noise sensor microphone and/or a printed circuit board thereof, especially in small and/or complex electronic equipment such as hearing protection devices, may be difficult or impossible for conventional hearing protection devices without significant disassembly of the hearing protection device, or may be completely impossible.

Systems, apparatuses, and methods disclosed herein generally relate to hearing protection devices and noise exposure sensor housings for the same. In some embodiments, a system can include an ear cup for a hearing protection device that defines an aperture on an exterior casing or other such surface. In some embodiments, the ear cup can further include a housing fixably disposed at or proximate the aperture and defining an axial bore therethrough. In some embodiments, the housing can have a proximal portion of the axial bore that is defined in part by a slot or ledge such that the proximal portion is configured to receive a microphone or other such sensor. In some embodiments, the housing can have a distal portion of the axial bore having an inner diameter that is less than the inner diameter of the proximal portion. In some embodiments, the ledge can be defined by the portion of the axial bore at the transition between the narrower distal portion and the wider proximal portion. In some embodiments, the ledge can be formed as a surface facing the proximal end of the housing. In some embodiments, the proximal portion of the axial bore can have a wider inner diameter at the transition point from the distal portion to the proximal portion, the transition point defining the ledge. In some embodiments, the inner diameter of the proximal portion can be smaller at one or more points proximal the transition point such that the slot is formed. In some embodiments, the slot can be the portion of the proximal portion or of the axial bore in general that has the largest inner diameter such that the noise sensor can be retained in that portion against axial movement by a reduced inner diameter both distal the slot and proximal the slot. In some embodiments, a narrower region of the proximal portion of the axial bore proximal the slot can be at least partially open in a radial direction, meaning a region of an outer wall of the housing aligned with the narrower region of the proximal portion can extend only part of the way around the axial bore, such that one or more components of the noise sensor can extend out radially from the proximal portion of the axial bore at a location proximal the slot. In some embodiments, the distal portion can be configured to receive ambient noise from the environment outside the ear cup and communicate that ambient noise to the microphone or other such sensor disposed and retained within the proximal portion (also known herein as the noise sensor receiving portion) of the housing. In some embodiments, the microphone or other such sensor disposed within the proximal portion of the housing can be connected to one or more printed circuit boards (PCB) having a somewhat planar structure or any other suitable form factor. In some embodiments, some or all of one or more PCBs may be flexible. In some embodiments, the one or more PCBs can include a microphone PCB operably coupled to the microphone or other such sensor and a flexible PCB operably connected to the microphone PCB.

In some embodiments, the ear cup can further include an internal dust protector disposed between the microphone and the housing at the proximal end of the distal portion of the axial bore such that the microphone can be exposed to ambient noise communicated through the distal portion of the axial bore without being exposed or with only slight exposure to contaminants such as dust from the environment outside the ear cup. In some embodiments, the ear cup can further include a removable securing collar disposed on and/or at or proximate the aperture of the external casing of the ear cup in such a way as to secure the housing at or proximate the aperture. In some embodiments, the removable securing collar can define an opening through a portion, such as the center, of the removable securing collar. In such a way, in some embodiments, the ambient noise from the environment outside the ear cup can be freely communicated through the opening of the removable securing collar, into the distal portion of the axial bore, and to the microphone or other such noise sensor assembly disposed within the proximal portion of the axial bore of the housing. In some embodiments, the ear cup can further include an external dust protector disposed within, on, or about the aperture of the external casing of the ear cup, between the distal end of the housing and the removable securing collar. In some embodiments, the internal dust protector and the external dust protector can together prevent contaminants such as dust and other debris common to construction sites and other similar environments from reaching the microphone and other electronics and circuitry within the ear cup.

In some embodiments, the ear cup can further include an ear pad dimensioned and configured to be sealably disposed to a wearer's head about a wearer's ears. In some embodiments, the ear pad can include or be made from a cushioning material, such as a deformable foam or rubber material such that ear pad has a noise dampening effect for the wearer when properly wearing the hearing protection device. In some embodiments, in addition to enclosing the wearer's ear within the ear cup and providing comfort, the ear pad can serve a similar purpose as the internal dust protector and/or the external dust protector, which is to at least reduce and possibly prevent the communication of dust and other contaminants into the ear cup, when properly worn by the wearer. In some embodiments, therefore, an interior space defined within the ear cup by at least the ear pad, the external casing of the ear cup, the housing disposed at or proximate the aperture of the external casing, and the microphone or other such sensor disposed within the proximal portion of the axial bore of the housing can be airtight or substantially airtight when properly worn by the wearer.

In some embodiments, the distal portion of the axial bore of the housing can be configured and dimensioned such that a noise sensor calibration tool can be securely inserted within the axial bore and sealed against the axial bore for microphone calibration by removing the removable securing collar, removing the external dust protector, and slideably disposing the noise sensor calibration tool into the axial bore via a distal opening of the axial bore. In some embodiments, securely engaging the noise sensor calibration tool within the axial bore for calibration of the microphone or other such noise sensor can ensure that ambient noise from the environment outside the ear cup is not detected by the microphone during calibration and that a calibrating noise emitted by the noise sensor calibration tool during in situ calibration of the microphone or other such noise sensor remains substantially within the axial bore and is not emitted to the interior space of the ear cup or the environment outside the ear cup. As such, in some embodiments, the microphone or other such noise sensor can be calibrated in place without significant disassembly of the hearing protection device and such that the space around the microphone is substantially airtight during calibration, increasing the accuracy of calibration.

In some embodiments, the housing may include a securing portion at the distal end of the housing that has a narrower portion relative to the outer diameter of the main body of the housing proximal the narrower portion and a wider portion distal the narrower portion. The securing portion, in combination with the remaining structure of the housing and casing, may ensure that the ear cup is airtight during operation. In some embodiments, an outer diameter of the narrower portion is dimensioned and configured to correspond substantially with an inner diameter of the aperture of the external casing of the ear cup or an intermediate component such as a contacting lip disposed proximate the aperture such that the housing can be inserted into the aperture and retained sealably in place when an outer surface of the narrower portion of the housing abuts an inner surface or an inner edge of the aperture. In some embodiments, the housing can be disposed within the ear cup without necessarily engaging the external casing of the ear cup. In some embodiments, the housing can be at least somewhat deformable such that the wider portion of the housing can be fit through the aperture of the external casing of the ear cup during assembly of the ear cup. In some embodiments, the ear cup can be assembled, at least in part, by temporarily deforming the wider portion at or near the distal end of the housing and fitting the wider portion through the aperture from the inside of the external casing of the ear cup, soldering or otherwise electrically coupling the microphone to the PCB, and disposing the microphone through an opening at the proximal end of the housing until the microphone comes to rest on the ledge or slot defined at a transition point where the proximal portion of the axial bore narrows to define a proximal end of the distal portion of the axial bore. In some embodiments, the housing can be a monolithic structure in order to facilitate the airtight nature of the interior region of the ear cup during use of the hearing protection device and the airtight nature of the axial bore during calibration of the microphone.

FIG. 1A-1D show a hearing protection device 10 according to an embodiment described herein. The hearing protection device 10 as illustrated in FIG. 1A includes a supporting band 105 connecting a first ear cup 100*a* to a second ear cup 100*b*. An ear cup 100*a,b* can comprise a structural cup lined with sound-dampening material (also known herein as an "ear pad") dimensioned and configured to engage a wearer's head about the wearer's ears such that the sound-dampening material sealably engages the wearer's head. As such, when properly worn, the hearing protection device 10 can be configured to prevent at least some of the ambient noise to which the wearer would otherwise be exposed if not wearing the hearing protection device 10 from reaching the wearer's ears. In some embodiments, each of the ear cups 100*a,b* of the hearing protection device 10 can further include a noise sensor assembly 110*a,b*. The first ear cup 110*a* and the second ear cup 100*b* can be similar to, a mirror image configurationally of, dissimilar to, or identical to one another. As such, the ear cups 100*a,b* are hereinafter referred generally as an ear cup 100 and components thereof will be referred to as a noise sensor assembly 110, a removable securing collar 111, and the like, without identifying a particular ear cup.

In some embodiments, the noise sensor assembly 110 can be positioned anywhere on or near the external surface of the ear cup 100 such that ambient noise from nearby the wearer's ear, external to the ear cups can be measured using the noise sensor assembly 110. This noise exposure signal can then be used in active noise cancellation to generate a destructively interfering audio signal that is generated via a processor and memory in one or both ear cups (e.g., on the main PCB of the ear cups) and output via the speakers shown in each ear cup. The noise exposure signal may additionally or alternatively be used to compare with a noise exposure signal from a microphone inside the ear cups to determine the drop in noise exposure between the exterior and interior of the ear cups (e.g., to confirm that the hearing protection device is working properly and is properly sealed and worn on the user's head). In some embodiments, the noise sensor assembly 110 can be positioned as close to the wearer's ear as possible, such as on an outer portion of the ear cup 100 near the sound-dampening material. Without wishing to be bound by any particular theory, placing the noise sensor assembly 110 on or in the ear cup 100 at a position sufficiently nearby the wearer's ear may increase the accuracy of the sensed noise relative to actual noise to which the wearer would be exposed were they not wearing the hearing protection device 10. In some embodiments, the hearing protection device 10 can further include a removable securing collar 111 disposed about the noise sensor assembly 110 and configured to retain the noise sensor assembly 110 at or proximate an aperture of the ear cup 100.

In some embodiments, the removable securing collar 111 can be disposed to an outer surface of the hearing protection device 10 and can be configured to span an aperture defined through the outer surface of the hearing protection device 10. In some embodiments, the removable securing collar 111 can be configured to the noise sensor assembly 110 on, within, or partially within the hearing protection device 10. In some embodiments, the removable securing collar 111 can include an opening dimensioned and configured to transmit sound therethrough to the noise sensor assembly 110. In some embodiments, the hearing protection device 10 can further include an external dust protector disposed between the noise sensor assembly 110 and the removable securing collar 111.

Figure 1B:
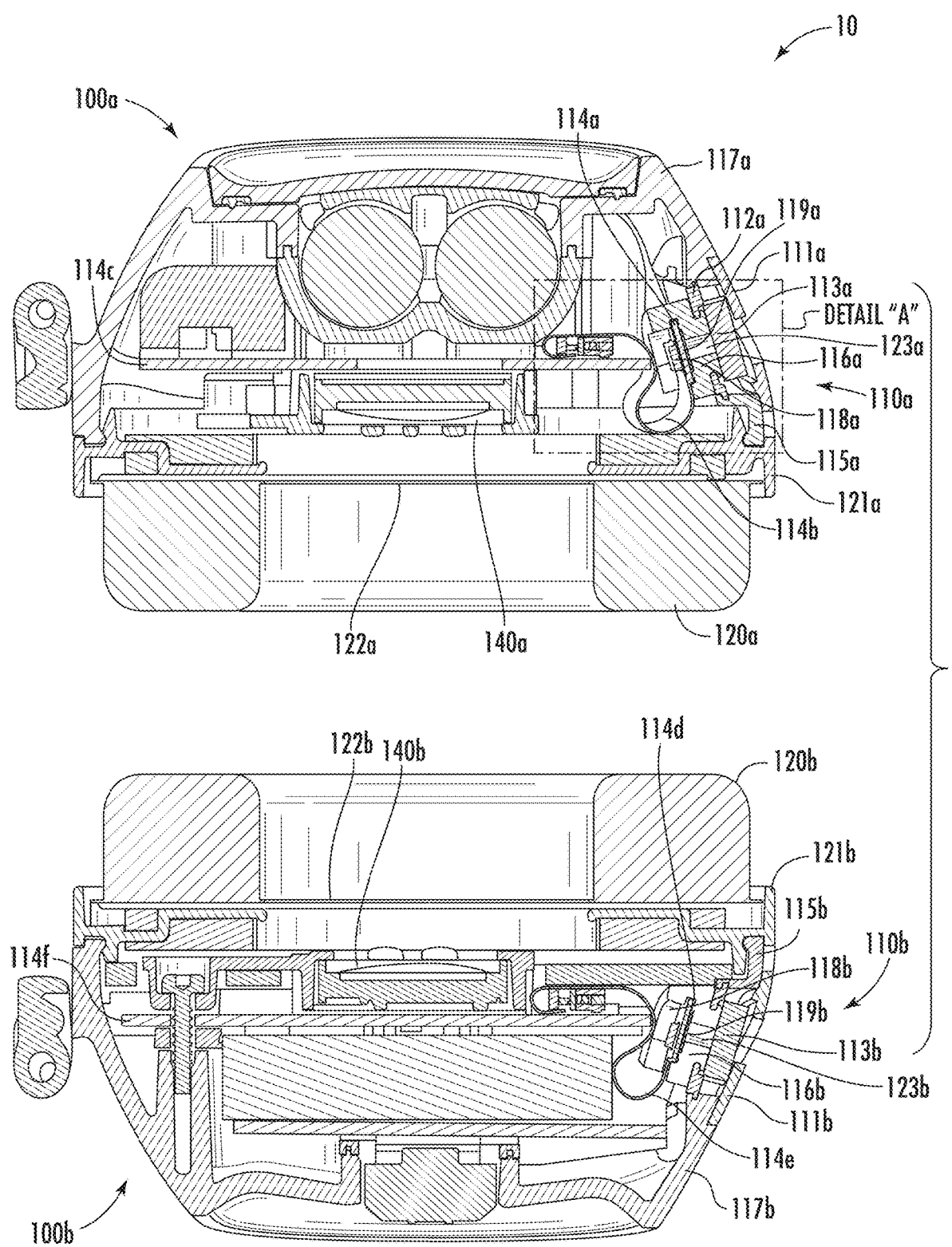
FIG. 1B shows a cut-away view of the hearing protection device of FIG. 1A, according to an embodiment of the present invention.
Figure 1C:
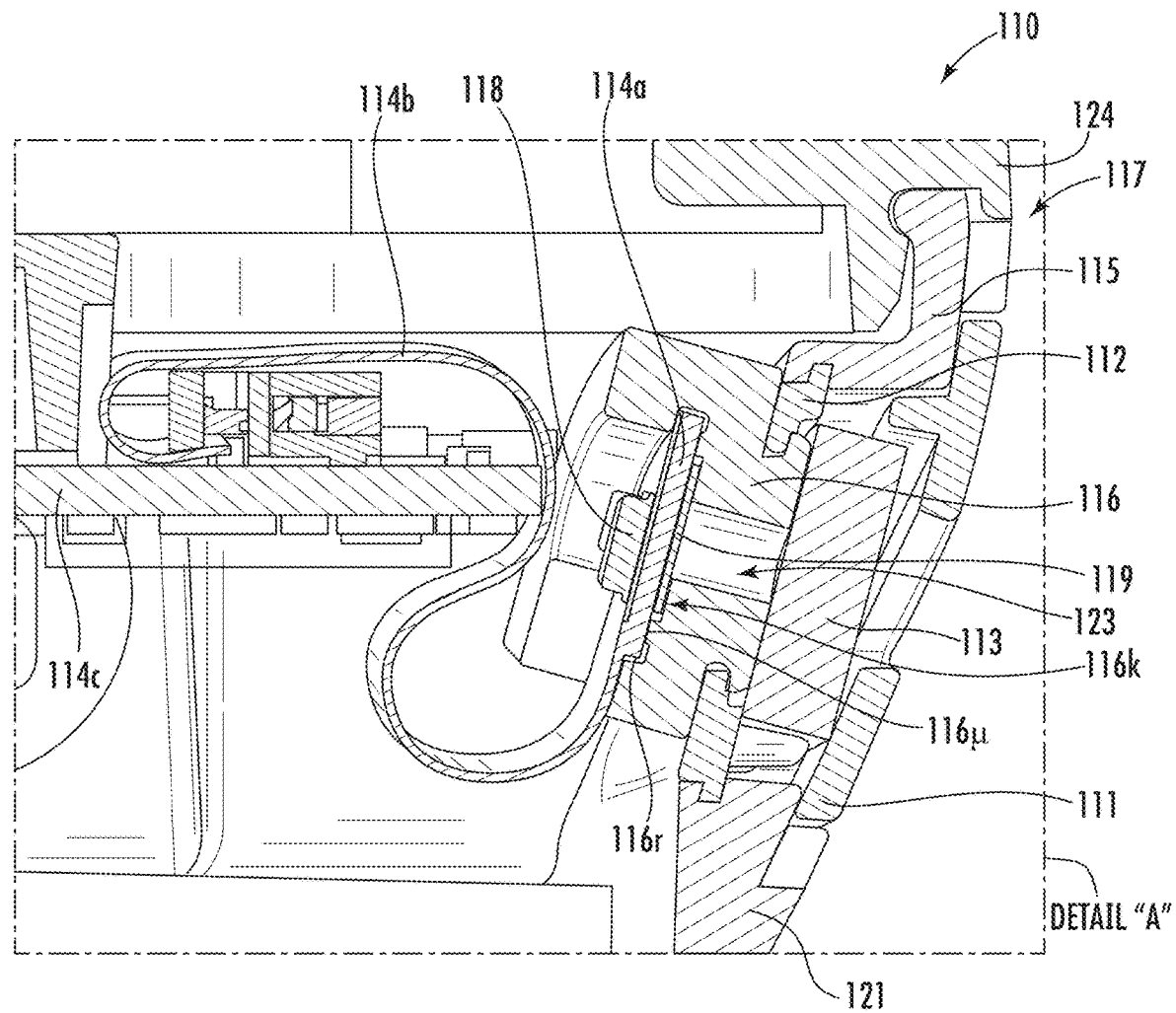
FIG. 1C shows a detail from the cut-away view of the hearing protection device shown in FIG. 1B, according to an embodiment of the present invention.

As illustrated in FIGS. 1B and 1C, the ear cup 100 can further include a noise sensor assembly 110 comprising a housing 116 (e.g., 116a, 116b) fixably disposed at or proximate the aperture and defining an axial bore 123a, 123b therethrough. In some embodiments, the housing 116 can have a proximal portion of the axial bore 123a, 123b that is defined in part by a slot or ledge (not shown) such that the proximal portion is configured to receive a microphone 118 or other such sensor. In some embodiments, the housing 116 can have a distal portion of the axial bore 123a, 123b having an inner diameter that is less than the inner diameter of the proximal portion. In some embodiments, the distal portion of the housing 116 can be configured to receive ambient noise from the environment outside the ear cup 100 and communicate that ambient noise to the microphone 118 or other such sensor disposed and retained within the proximal portion (also known herein as a noise sensor receiving portion 125) of the housing 116. In some embodiments, the microphone 118 or other such sensor disposed within the proximal portion of the housing 116 can be disposed on one of the sensor printed circuit boards 114a, 114d (sensor PCBs 114a, 114d) and may be connected to one or more flexible printed circuit boards 114b, 114e (flexible PCB 114b, 114e). In some embodiments, the one or more flexible PCBs 114b, 114e can be operably coupled to one or more main PCBs 114c, 114f.

In some embodiments, the noise sensor assembly 110 can further include an internal dust protector 119 disposed between the microphone 118 and the housing 116 at the proximal end of the distal portion of the axial bore 123a, 123b (e.g., disposed between the sensor PCB 114a or 114d and the ledge) such that the microphone 118 can be exposed to ambient noise communicated through the distal portion of the axial bore 123a, 123b of the housing 116 without being exposed or with only slight exposure to contaminants such as dust from the environment outside the ear cup 100.

In some embodiments, the ear cup 100 can further include the removable securing collar 111 disposed at or proximate the aperture defined through one or more components of a casing of the ear cup 100 in such a way as to secure the noise sensor assembly 110 within the ear cup 100 and as a way to access the noise sensor assembly 110 without disassembling the whole ear cup 100. The casing can comprise one or more of a first external casing portion 117, a second external casing portion 121, an insert catch 115 coupled to one or more of the first external casing portions 117, 121, and a contacting lip 112 coupled to the insert catch 115. Herein, the term "external casing" or "external casing 117" is used to refer to any one or any combination of these or similar elements configured to define or partly define the aperture through which the microphone 118 can be in acoustic communication with the environment outside the ear cup 100. In some embodiments, the hearing protection device 10 may be assembled at least in part by gluing or otherwise permanently adhering the ear pad 120a,b to the inside of the ear cup 100a,b, which can make it difficult to access the noise sensor assembly 110 by way of an inner surface 122a,b of the ear cup 100a,b. Likewise, the durability and air tightness of the ear cup 100 may be compromised if the ear cup 100 is opened along manufacturing lines, e.g., at a seam formed between the first and second portions of the external casing 117, 121 of the ear cup 100.

In some embodiments, the removable securing collar 111 can define an opening through a portion, such as the center, of the removable securing collar 111, by which the noise sensor assembly 110 can be accessed without significant disassembly of the ear cup 100 and without compromising the hearing protection characteristics of the hearing protection device 10. In some embodiments, the removable sealing collar 111 can further engage with the inset catch 115 of the external casing 117. The external casing 117 may be configured to carry or define the contacting lip 112 either as an integral piece or a separately inserted element. In some embodiments, the distal end of the housing 116 can be configured to rest on one or both of the inset catch 115 or the contacting lip 112 such that the removable securing collar 111 or a portion thereof can be fixedly inserted between the external dust protector 113 and the inset catch 115. As such, the external surface of the removable securing collar 111 can be flush or substantially flush with the outside surface of the external casing 117 of the ear cup 100.

In such a way, in some embodiments, the ambient noise from the environment outside the ear cup 100 can communicate through the opening of the removable securing collar 111, into the distal portion of the axial bore 123, and to the microphone 118 or other such noise sensor disposed within the proximal portion of the axial bore 123 of the housing 116. In some embodiments, the ear cup 100 can further include an external dust protector 113 disposed within, on, or about the aperture of the external casing 117 of the ear cup 100, between the distal end of the housing 116 and the removable securing collar 111. In some embodiments, the internal dust protector 119 and/or the external dust protector 113 can prevent contaminants such as dust and other debris common to construction sites and other similar environments from reaching the microphone 118 and other electronics and circuitry within the ear cup 100 while also preventing the axial bore 123 from becoming clogged and impairing the performance of the microphone 118.

In some embodiments, the ear cups 100a,b can further include ear pads 120a,b dimensioned and configured to be sealably disposed to a wearer's head about a wearer's ear. In some embodiments, the ear pad 120 can include or be made from a cushioning material, such as a deformable foam or rubber material such that the ear pad 120 has a noise dampening effect for the wearer when properly wearing the hearing protection device 10. In some embodiments, the ear pad 120 can serve a similar purpose as the internal dust protector 119 and/or the external dust protector 113, which is to at least reduce and possibly prevent the communication of dust and other contaminants into the ear cup 100, when properly worn by the wearer. In some embodiments, therefore, an interior space, defined within the ear cup 100 by at least the ear pad 120, the external casing 117 of the ear cup 100, the housing 116 disposed at or proximate the aperture of the external casing 117 of the ear cup 100, and the microphone 118, sensor PCB 114a, or other such sensor element disposed within the proximal portion of the axial bore 123 of the housing 116, can be airtight or substantially airtight when properly worn by the wearer to provide effective noise reduction for the wearer.

Figure 1D:
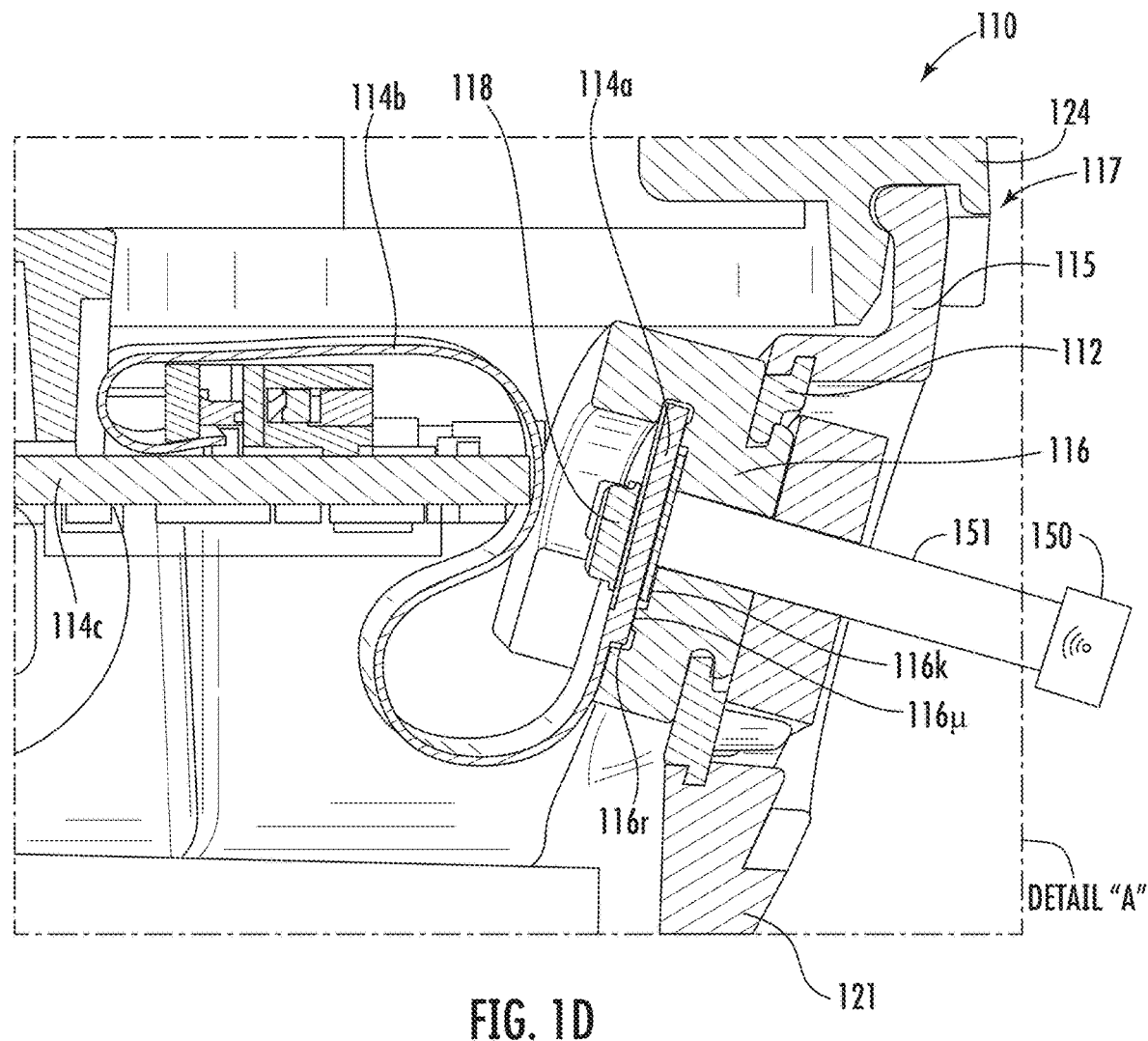
FIG. 1D illustrates an approach for calibrating a noise sensor for the hearing protection device shown in FIG. 1B, according to an embodiment of the present invention.
Figure 2A:
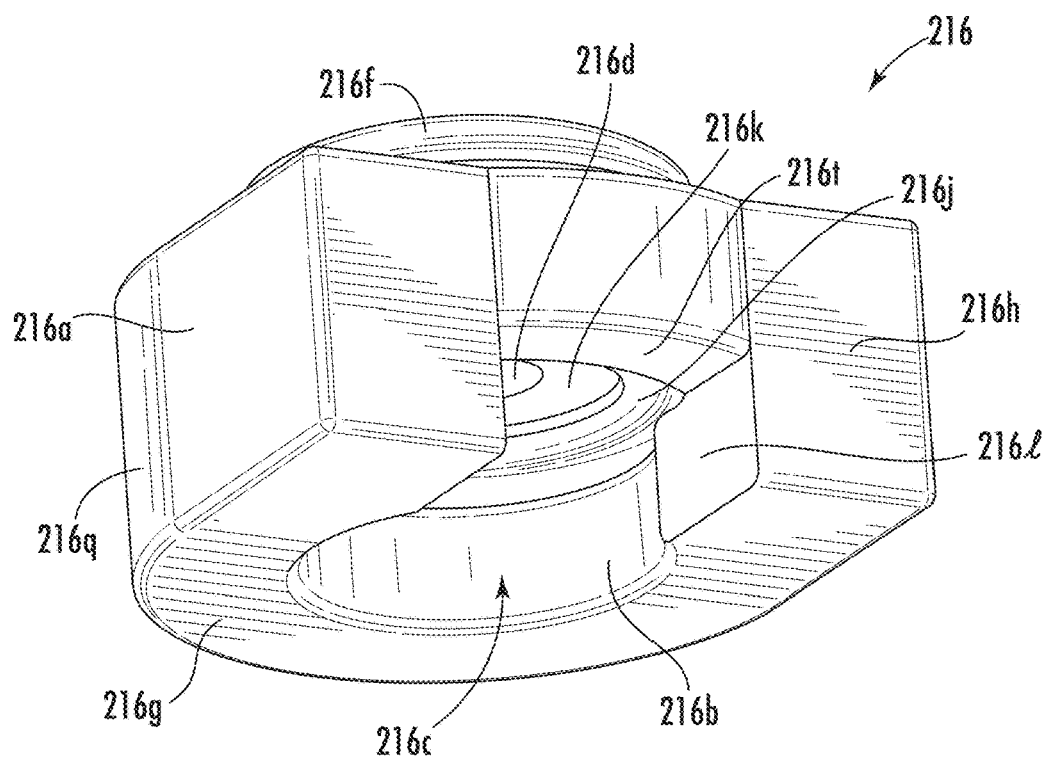
FIGS. 2A-2E show various views of a housing for noise sensor of a hearing protection device, according to an embodiment of the present invention.
Figure 2B:
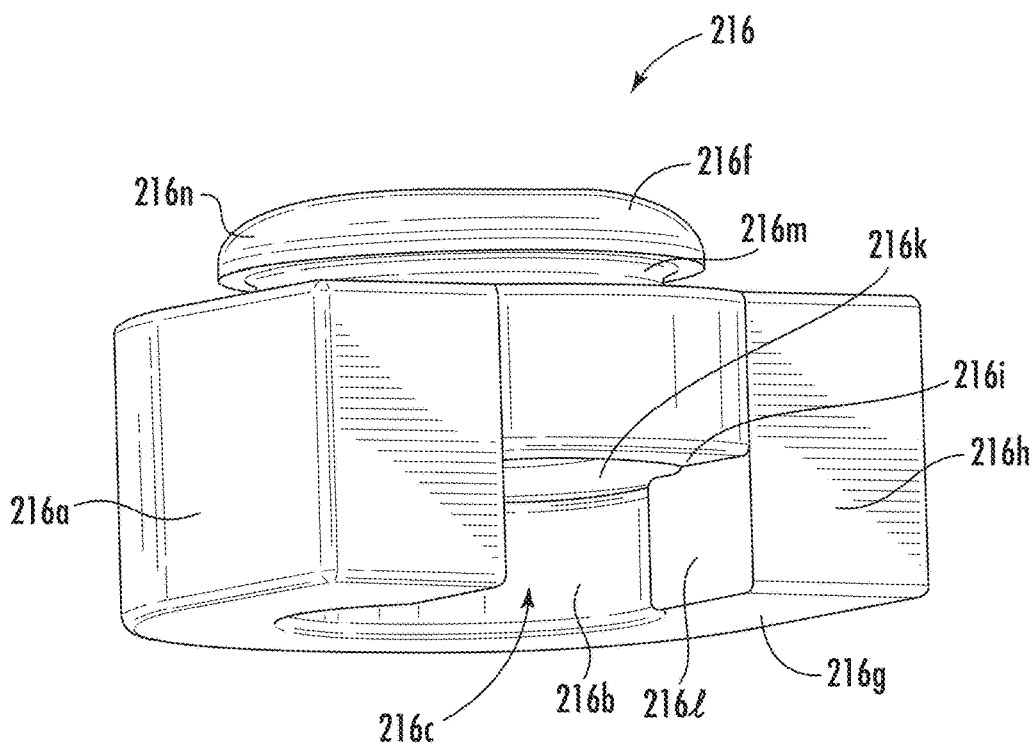
Figure 2C:
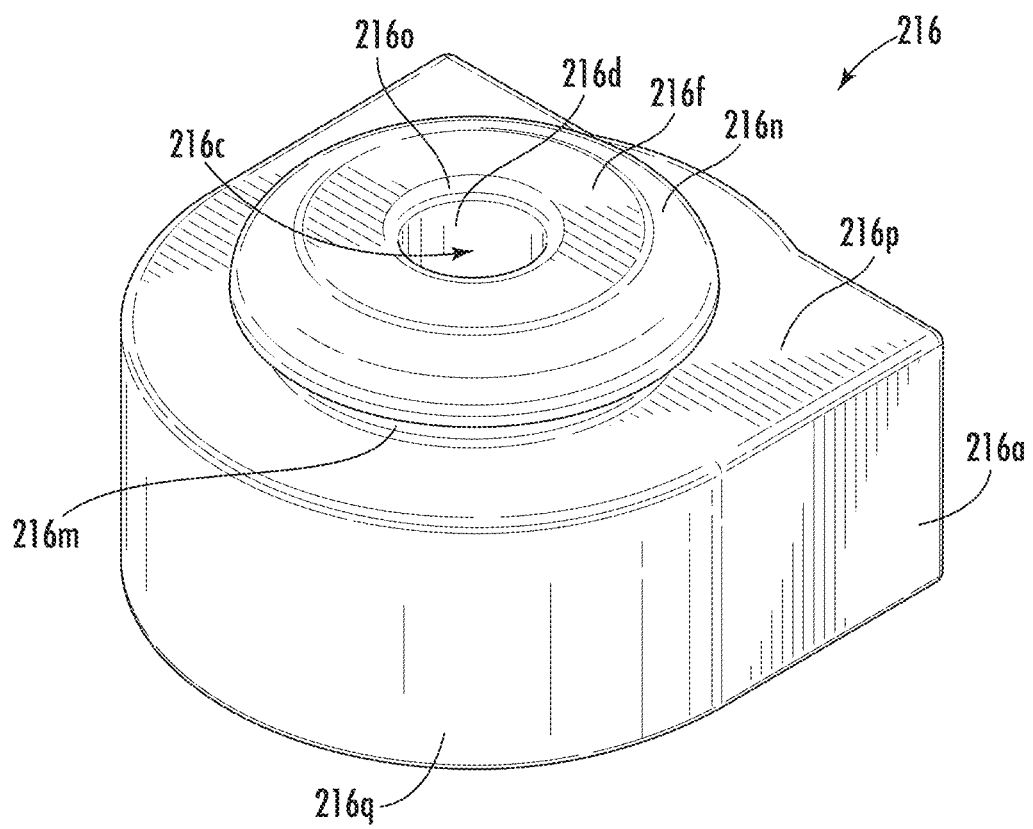
Figure 2D:
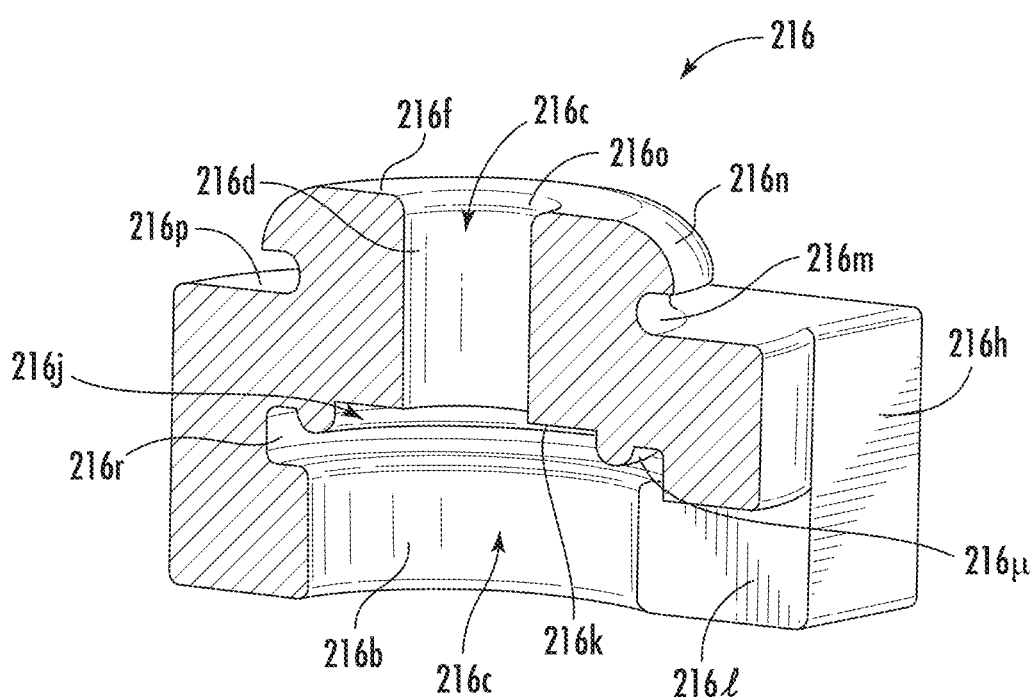
Figure 2E:
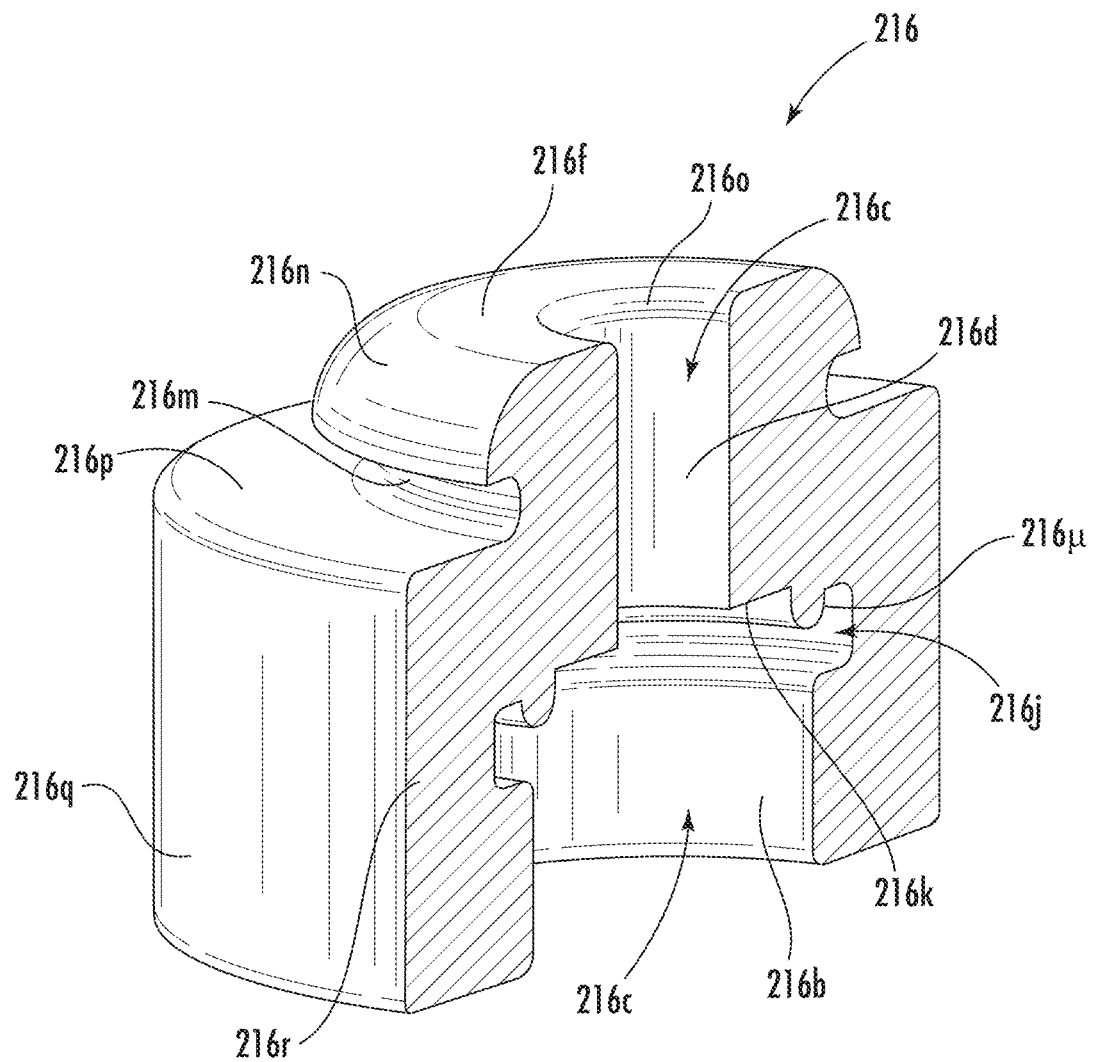
Figure 3A:
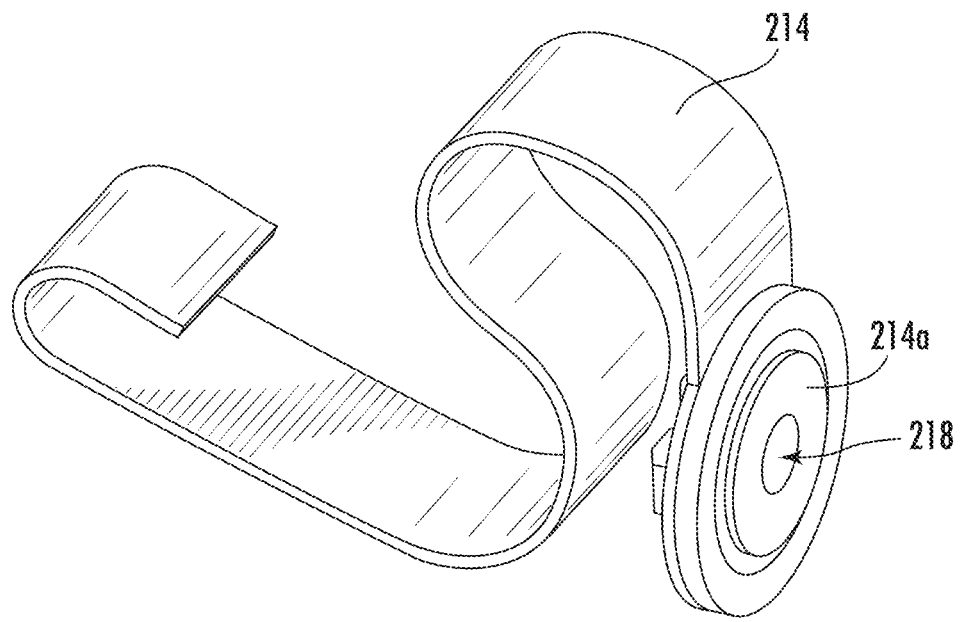
FIGS. 3A and 3B show various views of a noise sensor for a hearing protection device, according to an embodiment of the present invention.
Figure 3B:
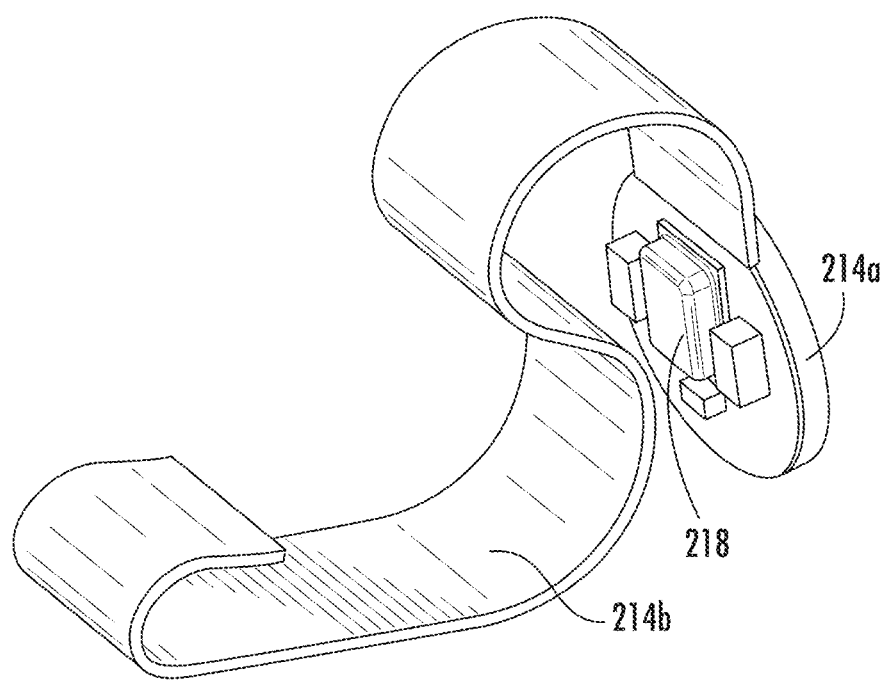

As illustrated in FIG. 1D, the distal portion of the axial bore 123 of the housing 116 can be configured and dimensioned such that a noise sensor calibration tool 150 comprising a calibration tube 151 can be securely fixed within the axial bore 123 for microphone 118 calibration by removing the removable securing collar 111, removing the external dust protector 113, and slideably disposing the noise sensor calibration tool 150 into the axial bore 123 via a distal opening of the axial bore 123 of the housing 116. In some embodiments, securely fixing the noise sensor calibration tool 150 or the calibration tube 151 within the axial bore 123 of the housing 116 for calibration of the microphone 118 or other such noise sensor can help prevent or reduce ambient noise from the environment outside the ear cup 100 being detected by the microphone 118 during calibration and that a calibrating noise emitted by the noise sensor calibration tool during in situ calibration of the microphone 118 or other such noise sensor remains substantially within the axial bore 123 of the housing 116 and is not emitted to the interior space of the ear cup 100 or the environment outside the ear cup 100. As such, in some embodiments, the microphone 118 or other such noise sensor can be calibrated in place without significant disassembly of the hearing protection device 10 and such that the space around the microphone 118 is substantially airtight during calibration, increasing the accuracy of calibration. For example, in some embodiments, the external dust protector 113 may be removed for calibration, while the internal dust protector 119 is left in place.

In some embodiments, such as when a hearing protection system and associated apparatus benefit from being airtight, during use and/or during calibration, it was found to be helpful to dimension and configure the housing 116 to have or define a securing portion at the distal end of the housing 116 that has a narrower portion relative to the outer diameter of the main body of the housing 116 proximal the narrower portion of the housing 116 and a wider portion of the housing 116 distal the narrower portion of the housing 116. In some embodiments, an outer diameter of the narrower portion of the housing 116 can be dimensioned and configured to correspond substantially with an inner diameter of the aperture of the external casing 117 of the ear cup 100 (or as applicable, a narrower opening in the external casing, such as the contacting lip 112 shown in FIG. 1C) such that the housing 116 can be inserted into the aperture of the external casing 117 and retained sealably in place when an outer surface of the narrower portion of the housing 116 abuts an inner surface or an inner edge at or proximate aperture of the external casing 117 to at least partially seal the aperture. In some embodiments, the housing 116 can be at least somewhat deformable such that the wider portion of the housing 116 can be fit through the aperture of the external casing 117 of the ear cup 100 during assembly of the ear cup. In some embodiments, the ear cup 100 can be assembled, at least in part, by temporarily deforming the wider portion of the housing 116 at or near the distal end of the housing 116 and fitting the wider portion of the housing 116 through the aperture of the external casing 117 of the ear cup 100 from the inside of the ear cup 100, soldering or otherwise electrically coupling the microphone 118 to the sensor PCB 114a, and disposing the microphone 118 through an opening at the proximal end of the housing 116 until the sensor PCB 114a comes to rest on the ledge or slot defined at a transition point where the proximal portion of the axial bore 123 of the housing 116 narrows to define a proximal end of the distal portion of the axial bore 123. In some embodiments, the housing 116 can be a monolithic structure in order to facilitate the airtight nature of the interior region of the ear cup 100 during use of the hearing protection device 10 and the airtight nature of the axial bore 123 of the housing 116 during calibration of the microphone 118.

In some embodiments, the external casing 117 of the hearing protection device 10 can include a first portion 121 and a second portion 124. In some embodiments, the first portion 121 and/or the second portion 124 can be configured to at least partially define the aperture. In some embodiments, the external casing 117 can be configured to sealably retain the removable securing collar 111 in the aperture. In some embodiments, the second portion 124 of the external casing 117 can be configured to be sealed to the first portion 121 such that at least a portion of the first portion 121 of the external casing 117, the second portion 124 of the external casing 117, the removable securing collar 111, the ear pad 120, and/or the housing 116 define the inner space of the ear cup 110 of the hearing protection device 10.

In some embodiments, the housing 116 can comprise an inner surface defining an axial bore 123. In some embodiments, a distal end of the axial bore 123 of the housing 116 can be configured to acoustically communicate with an external environment via the aperture defined in the external casing 117. In some embodiments, the housing 116 can define a noise sensor receiving portion 125 comprising a slot 116r, a ridge 116u, and/or a ledge 116k configured to engage at least a portion of the noise sensor assembly 110, such as the sensor PCB 114a and/or the microphone 118. In some embodiments, the proximal portion of the axial bore 123 can comprise or define the noise sensor receiving portion 125. In some embodiments, the noise sensor receiving portion 125 can be defined as a portion of the axial bore 123 between the proximal portion and the distal portion. In some embodiments, the slot 116r of the housing 116 can be configured to retain the noise sensor 110, such that the microphone 118 is configured to receive acoustic signals from the axial bore 123, e.g., the distal end of the axial bore 123. In some embodiments, in an instance in which the sensor PCB 114a is engaged with the housing 116, the sensor PCB 114a can be sealed against the housing 116 and the sensor PCB 114a and the housing 116 seal the aperture defined by the external casing 117 of the ear cup 100. In other words, in some embodiments, the housing 116 can be secured at or proximate the aperture of the external casing 117 and the microphone 118 and sensor PCB 114a can be secured within the noise sensor receiving portion 125 of the housing 116 such that ambient noise from outside the ear cup 100 can reach the microphone 118 by way of the axial bore 123 defined by the housing 116.

In some embodiments, the ear cup 100 can further include an interior region defined at least in part by the exterior casing 117 of the ear cup 100 and an ear pad 120 configured to contact a wearer's head about the wearer's ear. In some embodiments, the housing 116, in conjunction with the microphone 118 and the ear pad 120, can be configured such that the interior region of the ear cup 110 can be airtight or substantially air tight when the wearer is wearing the hearing protection device. In some embodiments, the ear cup 110 can further include a removable securing collar 111 configured to secure the housing 116 in place at or proximate the aperture of the external casing 117. In some embodiments, the removable securing collar 111 can define an opening through the middle or substantially through the middle of the removable securing collar 111 such that ambient noise can travel through the opening of the removable securing collar 111, into the axial bore 123 of the housing 116, and reach the microphone 118. In some embodiments, the ear cup 110 can further include an external dust protector 113 disposed between the distal end of the housing 116 and the removable securing collar 111. In some embodiments, the external dust protector 113 can be configured to impede the communication of debris such as dust, dirt, moisture, and the like into the housing 116 without impeding the audible communication of ambient noise to the microphone 118 during use of the hearing protection device.

In some embodiments, the removable securing collar 111 and/or external dust protector 113 can be removed in order to access the axial bore 123 for in situ calibration of the microphone 118. In other words, by removing the removable securing collar 111, the calibration tool 150 have a sufficient form factor can be slideably inserted into the axial bore 123 of the housing 116 such that a calibrating sounds can be emitted nearby the microphone 118. In some embodiments, the removable securing collar 111 may be engaged with the external casing 117 via one or more securing tabs or other interference fit structures, such that adhesives and permanent affixation elements are not required. In some embodiments, it can be helpful or even necessary to form an airtight or substantially airtight seal between the calibration tool 150 and the inner surface of the housing 116 such that the microphone 118 is not exposed to ambient noise in addition to the calibrating sound during calibration and so that the full measure of the calibrating sound reaches the microphone 118.

In some embodiments, the housing 116 can be configured to have suitable mechanical properties such that the microphone 118 is securely retained within the housing 116, while the housing 116 provides some amount of attenuation of vibrations caused by movement of the hearing protection device 10 by the wearer, by sound waves from nearby sound sources such as speakers and/or the environment outside the ear cup 100, and the like. For example, the housing 116 may be made of rubber or a rubber-like material. Furthermore, in some embodiments in which the housing 116 is a monolithic structure formed as a single piece or component, some benefits of the invention include a reduction in number and complexity of components required for noise sensing in the hearing protection device leading to a reduction in manufacturing cost and complexity, a reduction in probability of component failure, and a reduced occupied volume leading to a smaller possible ear cup 100 profile. Also, since the microphone 118 can be calibrated, the accuracy of noise detection will be improved. Furthermore, since the microphone 118 can be calibrated without significant disassembly of the ear cup 100, the cost, time, and complexity of calibration of the microphone 118 are reduced. Furthermore, since the axial bore 123 of the housing 116 is dimensioned and configured to slideably and sealably receive the standard calibration tool 150 during calibration of the microphone 118, the in situ calibration of the microphone 118 is more effective, meaning the accuracy of the calibrated microphone 118 for this hearing protection device 10 is greater than microphones of conventional hearing protection devices that are not able to be calibrated at all, not able to be calibrated after assembly of the hearing protection device, and/or can only be calibrated in less than airtight environments.

In some embodiments, the microphone 118, which can be any suitable type of microphone such as a microelectromechanical systems-(MEMS)-based microphone or the like, can be mounted on, fixed to, electrically coupled to, soldered to, and/or otherwise coupled to the sensor PCB 114a. In some embodiments, the sensor PCB 114a can be particularly dimensioned and configured such that a portion of the sensor PCB 114a can be retained, with the microphone 118, within the noise sensor receiving portion 125 of the housing 116. In some embodiments, the sensor PCB 114a can have any suitable form factor such that the sensor PCB 114a can sealably abut a surface of the noise sensor receiving portion 125 of the housing 116. For instance, the sensor PCB 114a can have a form factor that is substantially flat, planar, smooth, round, square, rectangular, quadrilateral, quadrangular, tubular, ellipsoidal, homogenous, even, symmetrical, asymmetrical, or the like. In some embodiments, the sensor PCB 114a or a portion thereof can be at least partially flexible. In some embodiments, the ear cup 100 can further comprise a main PCB 114c electrically connected via a flexible PCB 114b to the sensor PCB 114a, the sensor PCB 114a configured to be electrically coupled to the microphone 118. In some embodiments, the main PCB 114c may comprise a processor and memory for performing the signal processing of at least a portion of the hearing protection device, such as the examples described herein.

In some embodiments, the slot of the noise sensor receiving portion 125 of the housing 116 can define a volume having extents and dimensions that can be substantially inversely similar to the dimensions of the sensor PCB 114a such that the sensor PCB 114a can be securely disposed within the receiving portion of the housing 116 without adhesive or fasteners or otherwise securing the sensor PCB 114a within the housing other than by the relative dimensions of either. In some embodiments, the noise sensor receiving portion 125 of the housing 116 can be configured and dimensioned to releasably retain the noise sensor, comprising the sensor PCB 114a and the microphone 118, within the noise sensor receiving portion 125 of the housing 116. In other words, the particular dimensions of the noise sensor receiving portion 125 of the housing 116 can be particularly configured to retain the sensor assembly, comprising the sensor PCB 114a and the microphone 118, within the noise sensor receiving portion 125 of the housing 116, thereby forming an airtight seal between at least one of the sensor PCB 114a and the microphone 118, and the housing 116.

As such, when the noise sensor assembly 110 is properly assembled, air and noise from the environment outside the ear cup 100 can be communicated into the distal portion of the axial bore 123 of the housing 116 and to the microphone 118 and/or the sensor PCB 114a, but is prevented from communicating through the axial bore 123 past the microphone 118 and/or the sensor PCB 114a. As such, noise from the environment outside the ear cup 100 can be freely measured using the noise sensor assembly 110 but the interior space of the ear cup 100, including the proximal portion of the axial bore 123 of the housing 116 is not substantially exposed to the noise, air, contaminants, and the like from the environment outside the ear cup 100 due to the airtight seal and noise reduction technologies described herein.

In some embodiments, the exterior casing 117 of the ear cup 100 and the removable securing collar 111 can comprise or be formed from any suitably durable yet light material, such as a plastic material like acrylonitrile butadiene styrene (ABS) or the like. In some embodiments, the internal dust protector 119 can comprise or be formed from any suitable filtering material, such as Gore filtration material PE 120205 and other suitable ingress protection (IP) filter materials. In some embodiments, the internal dust protector 119 can be further configured to prevent flux of water between the distal portion of the axial bore 123 of the housing 116 and the noise sensor assembly disposed in the noise sensor receiving portion 125 proximate the distal portion of the axial bore 123 of the housing 116, thus preventing moisture damage to the sensor PCB 114a and/or the microphone 118. In some embodiments, the housing 116 can comprise or be formed from any suitably durable and yet deformable material, such as a synthetic rubber like ethylene propylene diene monomer (EPDM) rubber and the like. In some embodiments, the external dust protector 113 can comprise or be formed from any suitable dust filtering material such as a form, a mesh, a woven fiber, and the like.

In some embodiments, the ear cup 100 can further comprise an internal microphone 140 configured as a noise sensor to sense noise exposure within the inner space of the ear cup 100. For instance, the internal microphone 140 can be configured to measure noise from outside the ear cup 100 that is communicated into the inner space of the ear cup 100. As such, the hearing protection device 10 can be configured such that the noise sensor assembly 110, the internal microphone 140, other suitable computing devices and/or circuitry, or other devices can be caused to transmit and/or store noise exposure data during use of the hearing protection device 10. In some embodiments, a signal indicative of a magnitude of noise exposure can be transmitted from the microphone 118 and/or the internal microphone 140 to the main PCB 114c or other suitable computing devices or circuitry, a memory device, or the like. In some embodiments, the magnitude of noise exposure measured by the microphone 118 can be compared to the magnitude of noise exposure measured by the internal microphone 140 to determine the effectiveness of the active and/or passive noise dampening capabilities of the hearing protection device 10, to identify improper use by the wearer such as when an ear cup 100 is not properly fitted against the wearer's head about the wearer's ears, and to identify when a noise sensor is in need of calibration or is malfunctioning.

Referring now to FIGS. 2A-2E, an ear cup (e.g., 110) for a hearing protection device (e.g., 10) can include a housing 216 as illustrated, according to an embodiment of the present disclosure. Unless otherwise stated, the features of the housing 216 shown in FIGS. 2A-2E may be included in the depicted housing 116 in FIGS. 1B-1C, and vice versa. As illustrated, the housing 216 can be dimensioned and configured to be fixably disposed at or proximate an aperture defined through an external casing of the ear cup. The housing 216 can define an axial bore 216c therethrough between a proximal end 216g and a distal end (i.e., 216f). In some embodiments, the housing 116 can have a proximal portion 216b of the axial bore 216c that is defined in part by a slot 216r and/or ledge 216k such that the proximal portion 216b is configured to receive a microphone (e.g., 118) or other such sensor. In some embodiments, the housing 216 can comprise a distal portion 216d of the axial bore 216c having an inner diameter that is less than the inner diameter of the proximal portion 216b. In some embodiments, the ledge 216k can be defined by the portion of the axial bore 216c at the transition between the narrower distal portion 216d and the wider proximal portion 216b. In some embodiments, the ledge 216k can be formed as a surface facing the proximal end 216g of the housing 216 and configured to engage the microphone PCB. In some embodiments, the proximal portion 216b of the axial bore 216c can have a wider inner diameter at a transition point 216s from the distal portion 216d to the proximal portion 216b, the transition point 216s at least partly defining the ledge 216k. In some embodiments, the inner diameter of the proximal portion 216b can be smaller at one or more points proximal the transition point 216s such that the slot 216r is formed. In some embodiments, the slot 216r can be the portion of the proximal portion 216b or of the axial bore 216c in general that has the largest inner diameter such that the noise sensor can be retained in the slot 216r against movement in an axial direction by a reduced inner diameter both distal the slot and proximal the slot 216r. In some embodiments, a narrower region (e.g., defined by one or more internal surfaces 216e, 216t) of the proximal portion 216b of the axial bore 216c proximal the slot 216r can be at least partially open in a radial direction (e.g., a cutout in the side wall of the portion of the axial bore proximal to the slot), meaning, in some embodiments, a region of an outer wall (e.g., 216a, 216q, 216h) of the housing 216 aligned with the narrower region of the proximal portion 216b may extend only part of the way around the axial bore 216c, such that one or more components of the noise sensor can extend out radially from the proximal portion 216b of the axial bore 216c at a location proximal the slot 216r.

In some embodiments, the distal portion 216d of the housing 216 can be configured to receive ambient noise from the environment outside the ear cup and communicate that ambient noise to the microphone or other such sensor disposed and retained within the proximal portion 216b (or a portion thereof known herein as a noise sensor receiving portion 216r) of the housing 216. In some embodiments, the microphone or other such sensor disposed within the proximal portion of the housing 216 can be connected to a printed circuit board (PCB, e.g., the PCB 114a) having a suitable form factor such that at least a portion of the PCB is retained within a noise sensor receiving portion 216j of the axial bore 216c of the housing 216. In some embodiments, the proximal portion 216b can comprise or define the noise sensor receiving portion 216j. In some embodiments, the noise sensor receiving portion 216j can be defined as a portion of the axial bore 216c within the proximal portion 216b and adjacent the distal portion 216d. In some embodiments, the one or more PCBs can include a microphone PCB 114a operably coupled to the microphone 118 or other such sensor, a flexible PCB 114b operably connected to the microphone PCB 114a, and a main PCB 114c to which the flexible PCB 114b is operably coupled.

In some embodiments, the distal portion 216d of the axial bore 216c of the housing 216 can be configured and dimensioned such that a noise sensor calibration tool (e.g., 150) can be securely fixed within the axial bore 216c for microphone calibration slideably disposing the noise sensor calibration tool through the distal end of the axial bore 216d and towards the proximal portion 216b of the housing 216. In some embodiments, securely fixing the noise sensor calibration tool within the axial bore 216c of the housing 216 for calibration of the microphone or other such noise sensor can help prevent or reduce ambient noise from the environment outside the ear cup being detected by the microphone during calibration and can prevent or reduce emission of a calibrating noise emitted by the noise sensor calibration tool during in situ calibration of the microphone or other such noise sensor to outside the housing 216, such as to the interior space of the ear cup or the environment outside the ear cup.

As such, in some embodiments, the microphone or other such noise sensor can be calibrated in place without significant disassembly of the hearing protection device and such that the space around the microphone is substantially airtight during calibration, increasing the accuracy of calibration.

In some embodiments, such as when a hearing protection system and associated apparatus benefit from being airtight, during use and/or during calibration, it was found to be helpful to dimension and configure the housing 216 to have or define a securing portion 216n at or near the distal end of the housing 216, the securing portion 216n comprising a narrower portion 216m relative to the outer diameter of the main body of the housing 216 proximal the narrower portion of the securing portion 216n and a wider portion 216f of the securing portion 216n distal the narrower portion 216m of the securing portion 216n. In some embodiments, an outer diameter of the narrower portion 216m of the securing portion 216n can be dimensioned and configured to correspond substantially with an inner diameter of the aperture of the external casing of the ear cup or one or more intermediate components (e.g., the contacting lip 112) such that the housing 216 can be inserted into the aperture of the external casing and retained sealably in place when an outer surface of the narrower portion 216m of the securing portion 216n abuts an inner surface or an inner edge of the aperture of the external casing or other intermediate component at the aperture. In some embodiments, the housing 216 can be at least somewhat deformable such that the wider portion 216f of the securing portion 216n can be fit through the aperture of the external casing of the ear cup during assembly of the ear cup. In some embodiments, the ear cup can be assembled, at least in part, by temporarily deforming the wider portion 216f of the securing portion 216n at or near the distal end of the housing 216 and fitting the distal portion 216f of the housing 216 through the aperture of the external casing of the ear cup from the inside of the ear cup, soldering or otherwise electrically coupling the microphone to the PCB, and disposing the microphone and a portion of the PCB into the proximal end of the axial bore 216c of the housing 116 until the microphone and/or the portion of the PCB come(s) to rest in the slot 216r and/or on the ledge 216k, the ledge 216k defined as an internal surface perpendicular to the axial bore 216c and positioned at a transition point 216s where the proximal portion 216b of the axial bore 216c of the housing 216 narrows to define a proximal end of the distal portion 216d of the axial bore 216c. In some embodiments, the ledge 216k can comprise a ridge 216u raised above the surface of the ledge 216k in a proximal direction and configured to sealably engage at least one of the sensor PCB 114a and the microphone 118. In some embodiments, the housing 216 can be a monolithic structure in order to facilitate the airtight nature of the interior region of the ear cup during use of the hearing protection device and the airtight nature of the axial bore of the housing 216 during calibration of the microphone.

In some embodiments, the distal portion 216d of the axial bore 216c of the housing 216 can be configured to acoustically communicate with an external environment via the aperture defined in the external casing of the ear cup. In some embodiments, the housing 216 can define a noise sensor receiving portion 216j comprising the slot 216r, the ledge 216k and the ridge 216u, the slot 216r, the ledge 216k, and/or the ridge 216u configured to engage the PCB and/or the microphone of the noise sensor assembly. In some embodiments, the slot 216r and/or the ledge 216k of the housing 216 can be configured to retain the noise sensor, such that the microphone faces the axial bore, e.g., the distal end of the axial bore. In some embodiments, in an instance in which the noise sensor is engaged with the housing 216, the noise sensor can be sealed or substantially sealed against the housing 216 and the noise sensor and the housing 216 can be configured to seal the aperture defined by the external casing of the ear cup. In other words, in some embodiments, the housing 216 can be secured at or proximate the aperture of the external casing and the microphone and/or PCB can be secured within the noise sensor receiving portion 216j of the housing 216 such that ambient noise from outside the ear cup can reach the microphone by way of the distal portion 216d of the axial bore 216c.

In some embodiments, the distal portion 216d of the axial bore 216c of the housing 216 can be accessible for in situ calibration of the microphone either during normal use of the hearing protection device or after only removing minimal components, such as only the removable sealing collar or only the removable sealing collar and an external dust protector. In other words, in some embodiments, a calibration tool having a sufficient form factor can be slideably inserted into the axial bore 216c of the housing 216 such that a calibrating sound can be emitted nearby the microphone. In some embodiments, it can be helpful or even necessary to form an airtight or substantially airtight seal with the inner surface of the distal portion 216d of the axial bore 216c such that the microphone is not exposed to ambient noise in addition to the calibrating sound during calibration and so that the full magnitude of the calibrating sound reaches the microphone.

In some embodiments, the housing 216 can be configured to have suitable mechanical properties such that the microphone is securely retained within the housing 216, but that the housing 216 provides some amount of attenuation of vibrations caused by movement of the hearing protection device by the wearer, by sound waves from nearby sound sources such as speakers and/or the environment outside the ear cup, and the like. Furthermore, in some embodiments in which the housing 216 is a monolithic structure formed as a single piece or component, some benefits of the invention include a reduction in number and complexity of components required for noise sensing in the hearing protection device leading to a reduction in manufacturing cost and complexity, a reduction in probability of component failure, and a reduced occupied volume leading to a smaller possible ear cup profile. Also, since the microphone can be calibrated, the accuracy of noise detection will be improved. Furthermore, since the microphone can be calibrated without significant disassembly of the ear cup, the cost, time, and complexity of calibration of the microphone are reduced. Furthermore, since the axial bore of the housing 216 is dimensioned and configured to slideably and sealably receive standard calibration tools during calibration of the microphone, the in situ calibration of the microphone is more effective, meaning the accuracy of the calibrated microphone for this hearing protection device is greater than microphones of conventional hearing protection devices that are not able to be calibrated at all, not able to be calibrated after assembly of the hearing protection device, and/or can only be calibrated in less than airtight environments.

In some embodiments, the housing 216 comprises a rounded exterior surface 216q, one or more flat exterior surfaces 216a, 216h on the outside of the housing 216 oriented parallel to the axial bore 216c, and one or more other flat exterior surfaces 216g, 216p, 216i on the outside of the housing 216 oriented perpendicular to the axial bore 216c. In some embodiments, the rounded exterior surface 216q and/or the one or more flat exterior surfaces 216a, 216*h* may be configured to abut a portion or component of the ear cup. In some embodiments, the rounded exterior surface 216*q* and/or the one or more flat exterior surfaces 216*a*, 216*h* may be configured to abut a portion or component of the ear cup such that the housing 216 is prevented from rotation relative to an orientation of the rest of the ear cup. In some embodiments, the proximal portion 216*b* of the axial bore 216*c* of the housing 216 may comprise or be adjoining one or more flat interior surfaces 216*e* such that a cut-out is defined between the one or more flat interior surfaces 216*e* and through a portion of a flat exterior surface 216*h* or a rounded exterior surface 216*q*. In some embodiments, the PCB may be disposed within the noise sensor receiving portion 216*j* of the housing 216 along with the microphone, while another portion of the PCB extends from the axial bore 216*c*, through the cut-out portion of the flat exterior surface 216*h* or the rounded exterior surface 216*q* of the housing 216, and into the interior space of the ear cup such that the PCB can be electrically coupled to other electronic components such as another PCB, a microprocessor or the like. In some embodiments, the portions of the housing surrounding the cut-out may define a horseshoe shape to facilitate insertion of the PCB by separating or pulling apart the distal ends of the horseshoe shape (e.g., with pliers) to allow the microphone PCB to insert into the slot.

Referring now to FIGS. 3A-3D, a noise sensor assembly 210 can comprise at least a microphone 218 and a sensor printed circuit board (PCB) 214*a*. In some embodiments, the sensor PCB 214*a* can be electrically and/or operably coupled to the microphone 218. In some embodiments, the sensor PCB 214*a* can be electrically and/or operably coupled to a flexible PCB 214*b* and the flexible PCB 214*b* can be operably coupled to a main PCB 214*c*. In some embodiments, the noise sensor assembly 210 or a portion thereof can be disposed within a portion of the housing 216, such as the noise sensor receiving portion 216*j*. In some embodiments, the microphone 218 can be any suitable type of microphone such as a microelectro-mechanical systems-(MEMS)-based microphone or the like, can be mounted on, fixed to, electrically coupled to, soldered to, and/or otherwise coupled to the sensor PCB 214*a*. In some embodiments, the sensor PCB 214*a* can be particularly dimensioned and configured such that at least a portion of the sensor PCB 214*a* can be retained, with the microphone 218, within the noise sensor receiving portion 216*j* of the housing 216. In some embodiments, the sensor PCB 214*a* can have any suitable form factor such that the sensor PCB 214*a* can sealably abut a surface of the receiving portion of the housing 216. For instance, the sensor PCB 214*a* can have a form factor that is substantially flat, planar, smooth, round, square, rectangular, quadrilateral, quadrangular, tubular, ellipsoidal, homogenous, even, symmetrical, asymmetrical, or the like. In the embodiment depicted in FIGS. 3A-3B, the sensor PCB 214*a* forms a substantially circular shape corresponding to the shape of the slot 216*r* shown in FIG. 2A-2E. In some embodiments, the electrical components mounted to the sensor PCB 214*a* may be offset from the edges such that the housing 216 can grip the sensor PCB 214*a*.

In some embodiments, the noise sensor receiving portion 216*j* of the housing 216 can define a volume having extents and dimensions that can be substantially inversely similar to the dimensions of the sensor PCB 214*a* such that at least a portion of the sensor PCB 214*a* can be securely disposed within the receiving portion of the housing 216 without adhesive or fasteners or otherwise securing the sensor PCB 214*a* within the housing 214 other than by the relative dimensions of either. In some embodiments, the noise sensor receiving portion 216*j* of the housing 216 can be configured and dimensioned to releasably retain the noise sensor, comprising the sensor PCB 214*a* and the microphone 218, within the noise sensor receiving portion 216*j* of the housing 216 in a similar manner. In other words, the particular dimensions of the noise sensor receiving portion 216*j* of the housing 216 can be particularly configured to retain the sensor assembly, comprising the sensor PCB 214*a* and the microphone 218, within the noise sensor receiving portion 216*j* of the housing 216, thereby forming an airtight seal between at least one of the sensor PCB 214*a* and the microphone 218, and the housing 218.

In some embodiments, the sensor PCB 214*a* can have any suitable form factor such that the sensor PCB 214*a* can sealably abut a surface of the receiving portion of the housing 216. In some embodiments, the sensor PCB 214*a*, the flexible PCB 214*b* and/or the main PCB 214*c* can have a form factor that is substantially flat, planar, smooth, round, square, rectangular, quadrilateral, quadrangular, tubular, ellipsoidal, homogenous, even, symmetrical, asymmetrical, or the like. In some embodiments, the sensor PCB 214*a* or a portion thereof can be at least partially flexible. In some embodiments, the sensor PCB 214*a* can be electrically connected via the flexible PCB 216*b* to the main PCB 214*c* or other such computing device or circuitry, and the sensor PCB 214*a* can be electrically connected to the microphone 218.

As such, when the noise sensor assembly 210 is properly assembled, air and noise from the environment outside the ear cup can be communicated into the distal portion 216*d* of the axial bore 216*c* of the housing 216 and to the microphone 218 and/or the sensor PCB 214*a*, but is prevented from communicating through the axial bore 216*c* to locations proximal the microphone 218 and/or the sensor PCB 214*a*. As such, noise from the environment outside the ear cup can be freely measured using the noise sensor assembly 210 but the interior space of the ear cup, including the proximal portion 216*b* of the axial bore 216*c* of the housing 216 is substantially not exposed to the noise, air, contaminants, and the like from the environment outside the ear cup based upon the air tightness and noise reduction techniques described herein.

In some embodiments, the microphone 218 can comprise a silicon wafer having a movable membrane and a fixed back plate over a cavity in the base wafer. In some embodiments, the sensor back plate can have a stiff perforated structure. In some embodiments, the microphone 218 can be a microelectro-mechanical system (MEMS) microphone. Without wishing to be bound by any particular theory, in response to air movements related to noise exposure, the movable membrane of the microphone 218 can move, causing a change in a magnitude of a capacitance between the movable membrane and the fixed back plate, which can be converted by any suitable ASIC to an electrical signal. For instance, the ASIC can use a charge pump to place a fixed charge on the movable membrane of the microphone 218, and the ASIC can then measure voltage variations caused by capacitance changes related to movements of the movable membrane relative to the fixed back plate. While the microphone 218 can comprise the above-mentioned components according to some embodiments, the microphone 218 can comprise any suitable combination of components such that noise exposure can be sensed.

In some embodiments, the sensor PCB 214*a* and/or the flexible PCB 214*b* can comprise an insulated substrate supporting a plurality of electrical components and conductive tracks, and can be configured to communicate electrical signals and data between computing devices and other related circuitry. In some embodiments, the sensor PCB 214a can be configured to receive the electrical signal from the microphone 218, for example from the ASIC, the electrical signal indicative of the movement of the movable membrane of the microphone 218 in response to a magnitude of air movements related to a magnitude of noise exposure. While the sensor PCB 214a can comprise the above-mentioned components according to some embodiments, the sensor PCB 214a can comprise any suitable combination of components such that a signal received from the microphone 218 can be transmitted and/or interpreted relative to a magnitude of noise exposure sensed by the microphone 218.

To provide an overall understanding, certain illustrative embodiments have been described; however, it will be understood by one of ordinary skill in the art that the systems, apparatuses, and methods described herein can be adapted and modified to provide systems, apparatuses, and methods for other suitable applications and that other additions and modifications can be made without departing from the scope of the systems, apparatuses, and methods described herein.

The embodiments described herein have been particularly shown and described, but it will be understood that various changes in form and details may be made. Unless otherwise specified, the illustrated embodiments can be understood as providing exemplary features of varying detail of certain embodiments, and therefore, unless otherwise specified, features, components, modules, and/or aspects of the illustrations can be otherwise combined, separated, interchanged, and/or rearranged without departing from the disclosed systems or methods. Additionally, the shapes and sizes of components are also exemplary and unless otherwise specified, can be altered without affecting the scope of the disclosed and exemplary systems, apparatuses, or methods of the present disclosure.

Conventional terms in the field of electrochemical cells have been used herein. The terms are known in the art and are provided only as a non-limiting example for convenience purposes. Accordingly, the interpretation of the corresponding terms in the claims, unless stated otherwise, is not limited to any particular definition. Thus, the terms used in the claims should be given their broadest reasonable interpretation.

Although specific embodiments have been illustrated and described herein, it will be appreciated by those of ordinary skill in the art that any arrangement that is adapted to achieve the same purpose may be substituted for the specific embodiments shown. Many adaptations will be apparent to those of ordinary skill in the art. Accordingly, this application is intended to cover any adaptations or variations.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure and is submitted with the understanding that it will not be used to interpret or limit the scope or meaning of the claims.

In this Detailed Description, various features may have been grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments may be combined with each other in various combinations or permutations. The scope of the embodiments should be determined with reference to the appended claims, along with the full scope of equivalents to which such claims are entitled.

The invention claimed is:

1. A noise sensor assembly for a hearing protection device, the noise sensor assembly comprising:
    a noise sensor comprising a microphone electrically coupled to a printed circuit board (PCB); and
    a housing dimensioned and configured to be fixably disposed at or proximate an aperture defined in an outer surface of an external casing of the hearing protection device,
    wherein the housing comprises an inner surface defining an axial bore,
    wherein the axial bore of the housing is dimensioned and configured to slideably receive a calibration tool to form an airtight seal with the inner surface of the housing, wherein a distal end of the axial bore is configured to acoustically communicate with an external environment via the aperture, wherein the housing defines a noise sensor receiving portion comprising a slot configured to engage the PCB of the noise sensor, wherein the slot of the housing is configured to retain the noise sensor, such that the microphone faces the axial bore, and wherein, in an instance in which the noise sensor is engaged with the housing, the noise sensor is sealed against the housing.

2. The noise sensor assembly of claim 1, wherein the housing further defines a securing portion at a distal end, the securing portion adapted to contact and secure the housing with respect to a portion of the outer surface of the hearing protection device.

3. The noise sensor assembly of claim 1, further comprising:

an internal dust protector disposed between the noise sensor receiving portion of the housing and the noise sensor, and wherein the internal dust protector is disposed between the microphone and the axial bore.

4. The noise sensor assembly of claim 1, wherein the housing comprises at least one of a vibration attenuation material and a noise dampening material.

5. The noise sensor assembly of claim 1, wherein, in an instance in which the noise sensor is engaged with the housing, the noise sensor is retained within the noise senor receiving portion and abuts the slot.

6. A method for calibrating the noise sensor of the hearing protection device of claim 1, the method comprising:

disposing the calibration tool through the aperture via the axial bore of the housing such that an interior of the calibration tool and the microphone are part of a closed system;

emitting, by the calibration tool, a calibrating sound having predetermined sound characteristics;

receiving, using the microphone, one or more detected sound characteristics of the calibrating sound; and in an instance in which a comparison of the one or more detected sound characteristics of the calibrating sound received by the microphone and the sound characteristics of the calibrating sound is indicative of a calibration error, calibrating the noise sensor relative to the calibrating sound.

7. An ear cup for a hearing protection device, the ear cup comprising:

an external casing defining an aperture; and a noise sensor comprising a microphone electrically coupled to a printed circuit board (PCB) and a housing fixably disposed at or proximate the aperture defined by the external casing, wherein the housing comprises an inner surface defining an axial bore, wherein the axial bore of the housing is dimensioned and configured to slideably receive a calibration tool to form an airtight seal with the inner surface of the housing, wherein a distal end of the axial bore is configured to acoustically communicate with an external environment via the aperture, wherein the housing defines a noise sensor receiving portion comprising a slot configured to engage the PCB of the noise sensor, wherein the slot of the housing is configured to retain the noise sensor, such that the microphone faces the axial bore, and wherein, in an instance in which the noise sensor is engaged with the housing, the noise sensor is sealed against the housing, and the noise sensor and the housing seal the aperture defined by the external casing.

8. The ear cup of claim 7, further comprising:

a removable securing collar, wherein the external casing comprises a first portion and a second portion, the second portion defining the aperture configured to sealably retain the removable securing collar, the second portion configured to sealingly engage the first portion such that the first portion, the second portion, and the removable securing collar seal the aperture in the external casing.

9. The ear cup of claim 7, wherein the noise sensor receiving portion of the axial bore has a first inner diameter and the distal end portion of the axial bore has a second inner diameter less than the first inner diameter.

10. The ear cup of claim 7, further comprising a removable sealing collar configured to sealably retain the housing at or proximate the aperture defined by the external casing, the removable securing collar comprising an opening such that the distal end of the axial bore of the housing is configured to acoustically communicate with the external environment via the aperture of the external casing and the opening of the removable sealing collar.

11. The ear cup of claim 7, further comprising a removable sealing collar configured to be retained by the aperture.

12. The ear cup of claim 8, further comprising:

an external dust protector disposed between the housing and the removable securing collar.

13. The ear cup of claim 7, wherein the housing further comprises a securing portion disposed about the axial bore, the securing portion comprising a first securing portion at a distal end of the housing having a first outer diameter and a second securing portion proximal of the first securing portion, the second securing portion have a second outer diameter less than the first outer diameter, the first securing portion and the second securing portion defining a flange and recess configured to secure the housing relative to the external casing.

14. The ear cup of claim 13, wherein, in an instance in which the noise sensor is engaged with the housing and the housing is sealably disposed directly or indirectly at or proximate the aperture of the external casing of the ear cup, and the ear cup is sealably engaged to a wearer's head about the wearer's ear, an internal volume of the ear cup is substantially airtight.

* * * * *